United States Patent
Mertens et al.

(10) Patent No.: US 7,914,760 B2
(45) Date of Patent: Mar. 29, 2011

(54) CRYSTALLINE INTERGROWTH MATERIAL OF SILICOALUMINOPHOSPHATE HAVING TWO INTERGROWN PHASES

(75) Inventors: Machteld M. Mertens, Boortmeerbeek (BE); An Verberckmoes, Serskamp (BE); Marcel J. Janssen, Kessel-Lo (BE); Yun Feng Chang, Houston, TX (US); Luc R. M. Martens, Melae (BE); Stephen Neil Vaughn, Kingwood, TX (US); Kenneth Ray Clem, Humble, TX (US); Wilfried J. Mortier, Kessel-Lo (BE)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 12/576,062

(22) Filed: Oct. 8, 2009

(65) Prior Publication Data

US 2010/0028679 A1 Feb. 4, 2010

Related U.S. Application Data

(62) Division of application No. 11/072,830, filed on Mar. 4, 2005, now Pat. No. 7,622,624.

(60) Provisional application No. 60/559,619, filed on Apr. 5, 2004, provisional application No. 60/634,655, filed on Dec. 9, 2004.

(51) Int. Cl.
*C01B 25/36* (2006.01)
*C01B 25/45* (2006.01)
*B01J 21/12* (2006.01)
*B01J 27/18* (2006.01)
*B01J 27/182* (2006.01)

(52) U.S. Cl. .......... 423/305; 423/328.1; 423/328.2; 423/306; 423/600; 502/214; 502/238

(58) Field of Classification Search .......... 423/299, 423/328.1, 335, 600, 625, 328.2, 305, 306; 502/214, 263, 355, 238
See application file for complete search history.

(56) References Cited

U.S. PATENT DOCUMENTS

| 4,440,871 A | 4/1984 | Lok et al. |
|---|---|---|
| 5,279,810 A | 1/1994 | Calabro |
| 5,609,843 A | 3/1997 | Wendelbo |
| 6,090,289 A * | 7/2000 | Verduijn et al. ....... 210/644 |

(Continued)

FOREIGN PATENT DOCUMENTS

WO 03/040037 A1 5/2003

OTHER PUBLICATIONS

J. Chen et al., "SAPO-18 Catalysts and their Bronsted Acid Sites", Journal of Physical Chemistry, vol. 98, pp. 10216-10224 (1994).

(Continued)

*Primary Examiner* — H. (Holly) T Le
(74) *Attorney, Agent, or Firm* — Kevin M. Faulkner

(57) ABSTRACT

A silicoaluminophosphate molecular sieve is disclosed that comprises first and second intergrown phases of a CHA framework type and an AEI framework type, wherein said first intergrown phase has an AEI/CHA ratio of from about 5/95 to about 40/60 as determined by DIFFaX analysis, the second intergrown phase has an AEI/CHA ratio of about 30/70 to about as determined by DIFFaX analysis and said molecular sieve has a silica to alumina molar ratio ($Si/Al_2$) from about 0.13 to about 0.24.

9 Claims, 8 Drawing Sheets

U.S. PATENT DOCUMENTS

| | | | |
|---|---|---|---|
| 6,334,994 B1 | 1/2002 | Wendelbo et al. | |
| 6,812,372 B2 | 11/2004 | Janssen et al. | |
| 6,906,232 B2 * | 6/2005 | Levin et al. | 585/638 |
| 6,953,767 B2 * | 10/2005 | Janssen et al. | 502/214 |
| 7,011,810 B2 * | 3/2006 | Dakka et al. | 423/708 |
| 7,253,331 B2 * | 8/2007 | Martens et al. | 585/640 |
| 7,271,123 B2 * | 9/2007 | Chang et al. | 502/214 |
| 7,301,065 B2 * | 11/2007 | Vaughn et al. | 585/640 |
| 7,622,624 B2 * | 11/2009 | Mertens et al. | 585/640 |
| 2002/0165089 A1 | 11/2002 | Janssen et al. | |
| 2004/0064008 A1 | 4/2004 | Maurer et al. | |
| 2005/0096214 A1 | 5/2005 | Janssen et al. | |
| 2005/0233895 A1 * | 10/2005 | Mertens et al. | 502/214 |
| 2006/0079397 A1 * | 4/2006 | Mertens et al. | 502/214 |
| 2006/0079723 A1 * | 4/2006 | Mertens et al. | 585/639 |

OTHER PUBLICATIONS

J. Chen et al., "Silicoaluminophosphate Number Eighteen (SAPO-18): A New Microporous Solid Acid Catalyst", Catalysis Letters, vol. 28, pp. 241-248 (1994).

A.M. Prakash et al., "Synthesis of SAPO-34: High Silicon Incorporation in the Presence of Morpholine as Template" Journal of the Chemical Society, Faraday Transactions, vol. 90 (15), pp. 2291-2296 (1994).

Yan Xu et al., "The Synthesis of SAPO-34 and CoSAPO-34 from a Triethylamine-Hydrofluoric Acid-Water System", Journal of the Chemical Society, Faraday Transactions, vol. 86(2), pp. 425-429 (1990).

Breck, D.W., "The Synthetic Zeolites." in: *Zeolite Molecular Sieves* (New York, Tarrytown, 1974), pp. 245-284.

J. Chen et al., "Understanding the Bronsted Acidity of SAPO-5, SAPO-17, SAPO-18 and SAPO-34 and their Catalytic Performance for Methanol Conversion to Hydrocarbons", Studies in Surface Science and Catalysis, vol. 84, pp. 1731-1738, (1994).

O.B. Vistad, et al., "Identification of a Key Precursor Phase for Synthesis of SAPO-34 and Kinetics of Formation Investigated by In Situ X-Ray Diffraction", J. Phys. Chem. B.,2001, 105, pp. 12437-12447 (2001).

N.J. Tapp et al., "Synthesis of $AlPO_4$-11", Zeolites, May 1988, vol. 18, pp. 183-188.

M.M.J. Tracey et al., "A General Recursion Method for Calculating Diffracted Intensities from Crystals Containing Planar Faults", Proceedings of the Royal Chemical Society, London, A (1991), vol. 433, pp. 499-520.

* cited by examiner

```
1        74.89   Standard Deviation:   3.48    49% 10_90    Contribution
2        76.39   Standard Deviation:   5.40    50% 45_55    Contribution
3        25.01   Standard Deviation:   8.09    Background   Counts
4        -7.73   Standard Deviation:    .13    2Theta Shift (*0.02; None=1)
AEI/CHA  ........ 28./72.
Error in AEI(CHA)      .74
Error in AEI/CHA       .01   Ratio:    .38
SUM|Errors|/n        39.81
```

CRYSTALLINE INTERGROWTH MATERIAL OF SILICOALUMINOPHOSPHATE HAVING TWO INTERGROWN PHASES

CROSS REFERENCE TO RELATED APPLICATIONS

This application is a Divisional Application of, and claims priority to, U.S. Ser. No. 11/072,830 filed Mar. 4, 2005 now U.S. Pat. No. 7,622,624; and also claims the benefit of Provisional Application U.S. Ser. No. 60/559,619 filed Apr. 5, 2004 and U.S. Ser. No. 60/634,655 filed Dec. 9, 2004, the disclosures of each fully incorporated by reference.

FIELD OF INVENTION

This invention relates to a crystalline material comprising intergrowths of a CHA framework type molecular sieve and an AEI framework type molecular sieve, its synthesis and its use in the conversion of oxygenates, particularly methanol, to olefins, particularly ethylene and propylene.

BACKGROUND OF INVENTION

Light olefins, such as ethylene, propylene, butylenes and mixtures thereof, serve as feeds for the production of numerous important chemicals and polymers. Typically, $C_2$-$C_4$ light olefins are produced by cracking petroleum refinery streams, such as $C_3$+ paraffinic feeds. In view of the limited supply of competitive petroleum feeds, production of low cost light olefins from petroleum feeds is subject to waning supplies. Efforts to develop light olefin production technologies based on alternative feeds have therefore increased.

An important type of alternative feed for the production of light olefins is oxygenates, such as $C_1$-$C_4$ alkanols, especially methanol and ethanol; $C_2$-$C_4$ dialkyl ethers, especially dimethyl ether (DME), methyl ethyl ether and diethyl ether; dimethyl carbonate and methyl formate, and mixtures thereof. Many of these oxygenates may be produced from alternative sources by fermentation, or from synthesis gas derived from natural gas, petroleum liquids, carbonaceous materials, including coal, recycled plastic, municipal waste, or other organic material. Because of the wide variety of sources, alcohol, alcohol derivatives, and other oxygenates have promise as economical, non-petroleum sources for light olefin production.

The preferred process for converting an oxygenate feedstock, such as methanol, into one or more olefin(s), primarily ethylene and/or propylene, involves contacting the feedstock with a crystalline molecular sieve catalyst composition. Crystalline molecular sieves have a 3-dimensional, four-connected framework structure of corner-sharing [$TO_4$] tetrahedra, where T is any tetrahedrally coordinated cation. Among the known forms of molecular sieve are silicoaluminophosphate (SAPO) molecular sieves, which contain a three-dimensional microporous crystal framework structure of [$SiO_4$], [$AlO_4$] and [$PO_4$] corner sharing tetrahedral units.

SAPO-34 and SAPO-18 are crystalline silicoaluminophosphate molecular sieve materials that have been reported as suitable catalysts for a variety of important processes, including the production of light olefins from oxygenates, such as methanol. SAPO-34 belongs to the family of molecular sieves having the framework type of the zeolitic mineral chabazite (CHA). SAPO-18 belongs to the family of molecular sieves having the AEI framework type. Other molecular sieves with the AEI framework type are ALPO-18 and RUW-18.

The preparation and characterization of SAPO-34 have been reported in several publications, including U.S. Pat. No. 4,440,871; J. Chen et al. in "Studies in Surface Science and Catalysis", Vol. 84, pp. 1731-1738; U.S. Pat. No. 5,279,810; J. Chen et al. in "Journal of Physical Chemistry", Vol. 98, pp. 10216-10224 (1994); J. Chen et al. in "Catalysis Letters", Vol. 28, pp. 241-248 (1994); A. M. Prakash et al. in "Journal of the Chemical Society, Faraday Transactions" Vol. 90(15), pp. 2291-2296 (1994); Yan Xu et al. in "Journal of the Chemical Society, Faraday Transactions" Vol. 86(2), pp. 425-429 (1990).

The preparation and characterization of molecular sieves with AEI framework type have been reported in several publications, including U.S. Pat. No. 4,440,871; J. Chen et al. in "Studies in Surface Science and Catalysis", Vol. 84, pp. 1731-1738; U.S. Pat. No. 5,279,810; J. Chen et al. in "Journal of Physical Chemistry", Vol. 98, pp. 10216-10224 (1994); J. Chen et al. in "Catalysis Letters", Vol. 28, pp. 241-248 (1994); pp. 2291-2296 (1994); Yan Xu et al. in "Journal of the Chemical Society, Faraday Transactions" Vol. 86(2), pp. 425-429 (1990); and U.S. Pat. No. 5,609,843.

In the conversion of methanol to olefins, SAPO-34 exhibits relatively high product selectivity to ethylene and propylene, and low product selectivity to paraffins and olefins with four or more carbons. Catalysts containing SAPO-34 are thus particularly suited for the conversion of methanol to olefins. Despite its good performance, carbonaceous deposits, commonly referred to as coke, quickly form in the catalytic cages of SAPO-34. Eventually, the presence of too much coke clogs up the cages and deactivates the catalyst. Also, despite its low selectivity to paraffins, SAPO-34 still produces by-products. Separating by-products from the desired ethylene and propylene adds additional cost to the methanol to olefin conversion process. Therefore, there is a continuing need to find new molecular sieves that have good product selectivity and produce few by-products.

U.S. Pat. No. 6,334,994, incorporated herein by reference, discloses a silicoaluminophosphate molecular sieve, referred to as RUW-19, which is said to be an AEI/CHA mixed phase composition. In particular, RUW-19 is reported as having peaks characteristic of both CHA and AEI framework type molecular sieves, except that the broad feature centered at about 16.9 (2θ) in RUW-19 replaces the pair of reflections centered at about 17.0 (2θ) in AEI materials and RUW-19 does not have the reflections associated with CHA materials centered at 2θ values of 17.8 and 24.8. DIFFaX analysis of the X-ray diffraction pattern of RUW-19 as produced in Examples 1, 2 and 3 of U.S. Pat. No. 6,334,994 indicates that these materials are characterized by single intergrown phases of AEI and CHA framework type molecular sieves with AEI/CHA ratios of about 60/40, 65/35 and 70/30, respectively (see FIG. 2 attached herewith).

U.S. Pat. No. 6,812,372, incorporated herein by reference, discloses a silicoaluminophosphate molecular sieve, now indentified as EMM-2, comprising at least one intergrown phase of molecular sieves having AEI and CHA framework types, wherein said intergrown phase has an AEI/CHA ratio of from about 5/95 to 40/60 as determined by DIFFaX analysis, using the powder X-ray diffraction pattern of a calcined sample of said silicoaluminophosphate molecular sieve.

Prime olefin selectivity (POS), which equates to the total selectivity of ethylene and propylene in the product, and the prime olefin ratio (POR), which equates to the amount of ethylene divided by the amount of propylene in the product, are two of the main economic drivers in any oxygenate conversion process. In practice, even small changes in POS and/or POR have an enormous effect on the economics of a commercial process. According to the present invention, it has now been found that, for certain AEI/CHA intergrowth materials, there is an optimum range of silica/alumina ratio over which both the POS and POR are maximized when the materials are used in the conversion of oxygenates to olefins. In addition, these AEI/CHA intergrowth materials have been found to exhibit excellent hydrothermal stability.

SUMMARY

In one aspect, the invention resides in a silicoaluminophosphate molecular sieve comprising at least first and second intergrown phases of a CHA framework type and an AEI framework type, wherein said first intergrown phase has an AEI/CHA ratio of from about 5/95 to about 40/60 as determined by DIFFaX analysis, the second intergrown phase has an AEI/CHA ratio of about 30/70 to about 55/45 as determined by DIFFaX analysis and said molecular sieve has a silica to alumina molar ratio (Si/Al$_2$) from about 0.13 to about 0.24.

Conveniently, the silicoaluminophosphate molecular sieve has a silica to alumina molar ratio from about 0.15 to about 0.22, more preferably from about 0.17 to about 0.21, such as from about 0.18 to about 0.19.

Conveniently, said first intergrown phase has an AEI/CHA ratio of from about 5/95 to about 30/70, such as from about 5/95 to about 20/80, as determined by DIFFaX analysis.

In one embodiment, the second intergrown phase has an AEI/CHA ratio of from about 35/65 to about 54/46, preferably from about 40/60 to about 53/47, and more preferably from about 45/55 to about 50/50.

The overall AEI/CHA ratio, which is the weighed average of all the intergrowth phases, preferably ranges from about 20:80 to about 40:60, more preferably from about 25:75 to about 35:65.

Conveniently, the weighed average AEI/CHA ratio of the first intergrown phase to the second intergrown phase is from about 10:90 to about 90:10, preferably from about 25:75 to about 75:25. Preferably, in its calcined form, the molecular sieve has an XRD pattern that exhibits two broad features in the 16 to 18.5 2θ range.

Conveniently, the silicoaluminophosphate molecular sieve retains at least 40%, such as at least 45%, of its activity for the conversion of methanol to ethylene and propylene after being treated at 700° C. for 30 days in a nitrogen atmosphere comprising steam at a partial pressure of 13 psi (90 kPa).

In a further aspect, the invention resides in a method of synthesizing a silicoaluminophosphate molecular sieve comprising at least first and second intergrown phases of a CHA framework type and an AEI framework type, wherein said first intergrown phase has an AEI/CHA ratio of from about 5/95 to about 40/60 as determined by DIFFaX analysis, the second intergrown phase has an AEI/CHA ratio of about 30/70 to about 55/45 as determined by DIFFaX analysis and said molecular sieve has a silica to alumina molar ratio (Si/Al$_2$) from about 0.13 to about 0.24, the method comprising:

(a) preparing a mixture comprising a source of water, a reactive source of silicon, a reactive source of aluminum, a reactive source of phosphorus and an organic directing agent for directing the formation of said molecular sieve such that said mixture has a molar composition within the following ranges:

P$_2$O$_5$: Al$_2$O$_3$ from about 0.6 to about 1.2,
SiO$_2$: Al$_2$O$_3$ from about 0.10 to about 0.20,
H$_2$O: Al$_2$O$_3$ from about 25 to about 50, (b) mixing and heating said mixture continuously to a crystallization temperature, typically between about 150° C. and about 200° C., preferably between about 155° C. and about 180° C.;

(c) maintaining said mixture at said crystallization temperature for a period of time from about 2 to about 150 hours; and (d) recovering said molecular sieve.

Conveniently, the heating in (b) is conducted so as to raise the temperature of said mixture at a rate of at least 8° C./hour, such as from about 10° C./hour to about 40° C./hour.

Preferably, the molar ratio of organic directing agent (also sometimes referred to as template) to alumina is from about 0.6 to about 1.2, more preferably from about 0.7 to about 1.1. Conveniently, said organic directing agent comprises a tetraethylammonium compound.

In yet a further aspect, the invention resides in a process for making an olefin product from an oxygenate feedstock comprising contacting said oxygenate feedstock with a catalyst comprising a silicoaluminophosphate molecular sieve of the invention.

BRIEF DESCRIPTION OF THE DRAWINGS

FIG. 6 also overlays DIFFaX simulated patterns.

DETAILED DESCRIPTION OF THE EMBODIMENTS

Figure 1A:
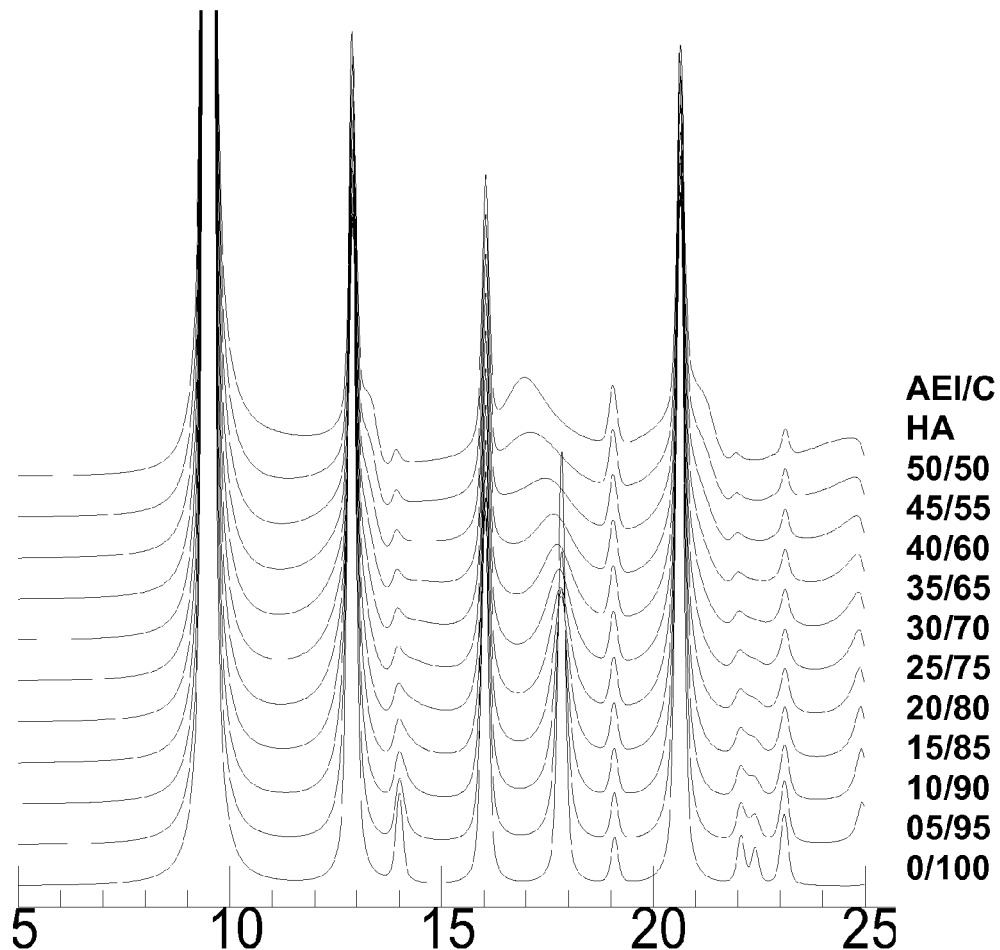
FIGS. 1a and 1b are DIFFaX simulated diffraction patterns for intergrown AEI/CHA phases having varying AEI/CHA ratios, using the simulation parameters disclosed in U.S. Pat. No. 6,812,372, but with a line broadening parameter of 0.04 in place of 0.009.

The present invention relates to a silicoaluminophosphate molecular sieve comprising at least first and second intergrown phases of a CHA framework type material and an AEI framework type material, wherein said first intergrown phase has an AEI/CHA ratio of from about 5/95 to about 40/60 as determined by DIFFaX analysis, the second intergrown phase has an AEI/CHA ratio of about 30/70 to about 55/45 as determined by DIFFaX analysis and said molecular sieve has a silica to alumina molar ratio (Si/Al$_2$) from about 0.13 to about 0.24 In addition, the invention relates to the synthesis of this novel intergrowth and to its use in a process for the conversion of oxygenates, particularly methanol, to olefins, particularly ethylene and propylene.

Intergrown molecular sieve phases are disordered planar intergrowths of molecular sieve frameworks. Reference is directed to the "Catalog of Disordered Zeolite Structures", 2000 Edition, published by the Structure Commission of the International Zeolite Association and to the "Collection of Simulated XRD Powder Patterns for Zeolites", M. M. J. Treacy and J. B. Higgins, 2001 Edition, published on behalf of the Structure Commission of the International Zeolite Association for a detailed explanation on intergrown molecular sieve phases.

Regular crystalline solids are built from structurally invariant building units, called Periodic Building Units, and are periodically ordered in three dimensions. Structurally disordered structures show periodic ordering in dimensions less than three, i.e. in two, one or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistical stacking sequences.

The silicoaluminophosphate molecular sieves described herein are disordered planar intergrowth of end-member structures AEI and CHA. For AEI and CHA framework types, the Periodic Building Unit is a double six ring layer. There are two types of layers "a" and "b", which are topologically identical except "b" is the mirror image of "a". When layers of the same type stack on top of one another, i.e. aaa or bbb, the framework type CHA is generated. When layers "a" and "b" alternate, ie. abab, the framework type AEI is generated. The molecular sieves described herein comprise stackings of layers "a" and "b" containing regions of CHA framework type and regions of AEI framework type. Each change of CHA to AEI framework type is a stacking disorder or planar fault.

In the case of crystals with planar faults, the interpretation of X-ray diffraction patterns requires an ability to simulate the effects of stacking disorder. DIFFaX is a computer program based on a mathematical model for calculating intensities from crystals containing planar faults (see M. M. J. Tracey et al., Proceedings of the Royal Chemical Society, London, A [1991], Vol. 433, pp. 499-520). DIFFaX is the simulation program selected by and available from the International Zeolite Association to simulate the XRD powder patterns for intergrown phases of zeolites (see "Collection of Simulated XRD Powder Patterns for Zeolites" by M. M. J. Treacy and J. B. Higgins, 2001, Fourth Edition, published on behalf of the Structure Commission of the International Zeolite Association). It has also been used to theoretically study intergrown phases of AEI, CHA and KFI, as reported by K. P. Lillerud et al. in "Studies in Surface Science and Catalysis", 1994, Vol. 84, pp. 543-550.

Figure 1B:
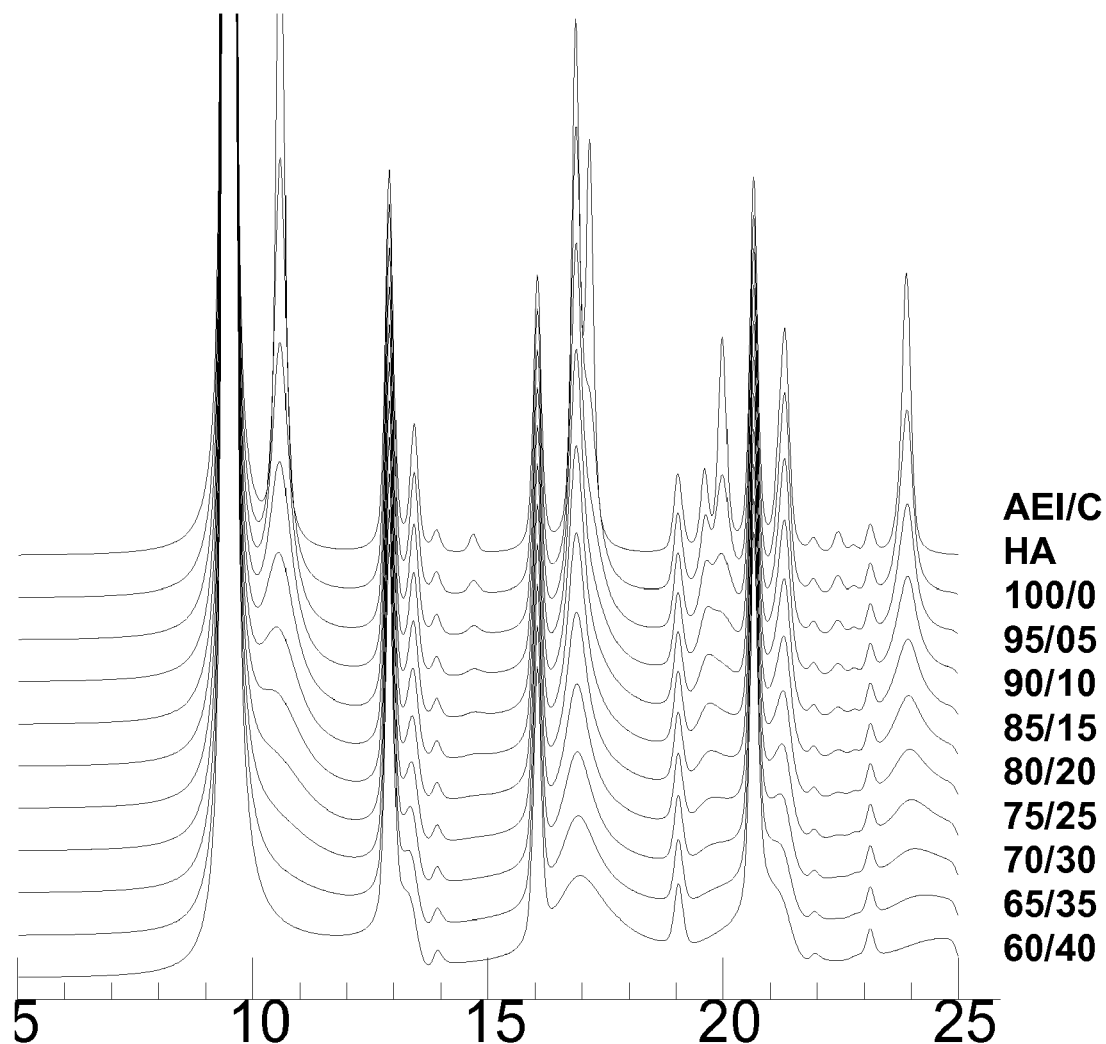

FIGS. 1a and 1b show the simulated diffraction patterns obtained for single intergrown phases having various AEI/CHA ratios. These patterns were calculated using the model parameters disclosed in U.S. Pat. No. 6,812,372, except a line broadening parameter of 0.04 was used instead of 0.009. All XRD diffraction patterns are normalized to the highest peak of the entire set of simulated patterns, i.e. the peak at about 9.6 degrees 2θ. Normalization of intensity values allows for the comparison between diffraction patterns of the intensity of an X-ray diffraction peak at a certain 2θ value.

As the ratio of AEI increases relative to CHA in a single intergrown phase, one can observe a decrease in intensity of certain peaks and an increase in intensity of other peaks. Intergrown phases with AEI/CHA ratios of 50/50 and above (AEI/CHA≧1.0) show a broad feature centered at about 16.9 (2θ). Intergrown phases with AEI/CHA ratios of 40/60 and lower (AEI/CHA≦0.67) show a broad feature centered at about 18 (2θ).

Figure 2:
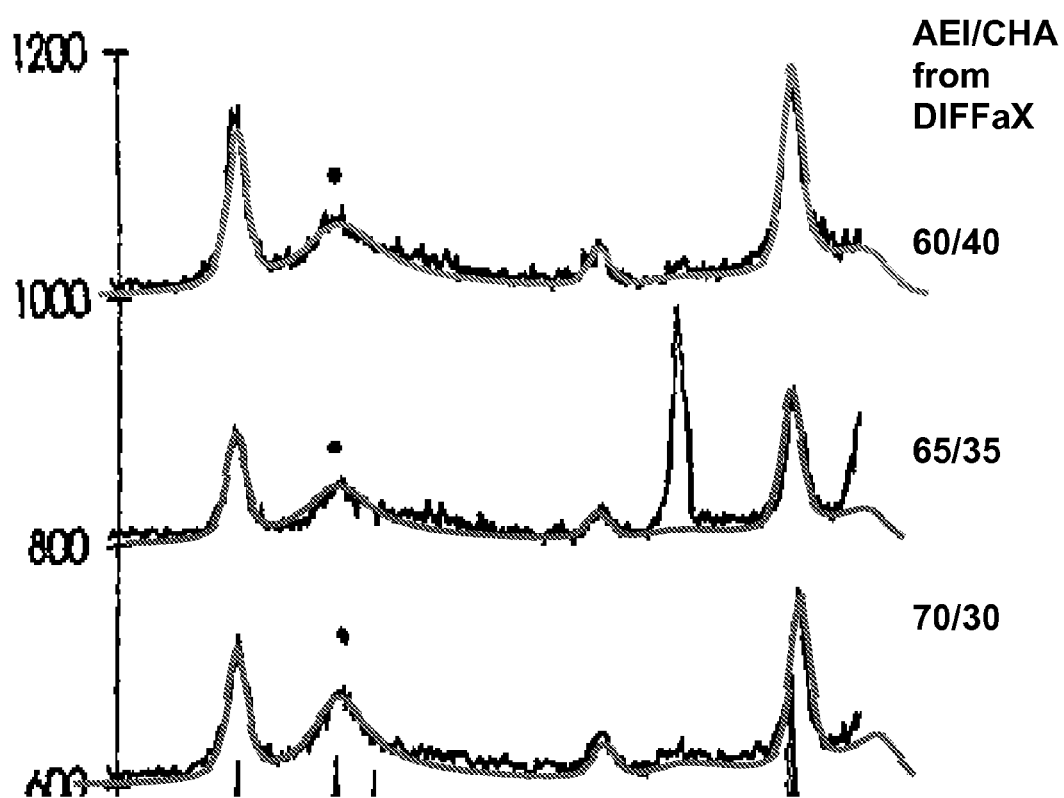
FIG. 2 shows an overlay of an enlarged portion of FIG. 1 of U.S. Pat. No. 6,334,994 with DIFFaX simulated patterns for single intergrown AEI/CHA phases having varying AEI/CHA ratios.

FIG. 2 shows an enlargement of the top three XRD patterns of FIG. 1 of U.S. Pat. No. 6,334,994, which correspond to the materials prepared in Examples 1, 2 and 3 of U.S. Pat. No. 6,334,994. These XRD patterns have been overlaid with the XRD patterns simulated by DIFFaX as described above. DIFFaX analysis indicates that the materials of Examples 1, 2 and 3 have an AEI/CHA ratio of 60/40, 65/35 and 70/30, respectively, taking into account the fact that the materials of Examples 2 and 3 are said to be contaminated with impurities. The materials of Examples 1, 2 and 3 of U.S. Pat. No. 6,334,994 all have a broad feature centered at about 16.9 (2θ).

The silicoaluminophosphate of the present invention is characterized by a powder XRD diffraction pattern (obtained from a sample after calcination and without rehydration after calcination) having at least the reflections in the 5 to 25 (2θ) range as shown in Table below:

TABLE 1

| 2θ (CuKα) |
| --- |
| 9.3-9.6 |
| 12.7-13.0 |
| 13.8-14.0 |
| 15.9-16.1 |
| 17.7-18.1 |
| 18.9-19.1 |
| 20.5-20.7 |
| 23.7-24.0 |

The X-ray diffraction data referred to herein are collected with a SCINTAG X2 X-Ray Powder Diffractometer (Scintag Inc., USA), using copper K-alpha radiation. The diffraction data are recorded by step-scanning at 0.02 degrees of two-theta, where theta is the Bragg angle, and a counting time of 1 second for each step. Prior to recording of each experimental X-ray diffraction pattern, the sample must be in the anhydrous state and free of any template used in its synthesis, since the simulated patterns are calculated using only framework atoms, not water or template. Given the sensitivity of silicoaluminophosphate materials to water at recording temperatures, the molecular sieve samples are calcined after preparation and kept moisture-free according to the following procedure.

About 2 grams of each molecular sieve sample are heated in an oven from room temperature under a flow of nitrogen at a rate of 3° C./minute to 200° C. and, while retaining the nitrogen flow, the sample is held at 200° C. for 30 minutes and the temperature of the oven is then raised at a rate of 2° C./minute to 650° C. The sample is then retained at 650° C. for 8 hours, the first 5 hours being under nitrogen and the final 3 hours being under air. The oven is then cooled to 200° C. at 30° C./minute and, when the XRD pattern is to be recorded, the sample is transferred from the oven directly to a sample holder and covered with Mylar foil to prevent rehydration. It is also possible after cool-down to room temperature, to do a fast recording of the XRD pattern immediately after removal of the Mylar foil (e.g. by using a total scan time of less than 5 minutes).

As can be seen from Table 1, the XRD diffraction patterns of the intergrown phases of AEI/CHA according to the present invention are characterized by the absence of peaks in the 9.8 to 12.0 (2θ) range, more particularly by the absence of peaks in the 10.0 to 11.0 (2θ) range, especially by the absence of peaks in the 10.4 to 10.6 (2θ) range. A further characteristic is the presence of a peak in the 17.7 to 18.1 (2θ) range. The reflection peak in the 17.7 to 18.1 (2θ) range has a relative intensity between 0.09 and 0.4, preferably between 0.1 and 0.35 with respect to the reflection peak at 17.9 (2θ) in the diffraction pattern of SAPO-34.

Figure 6:
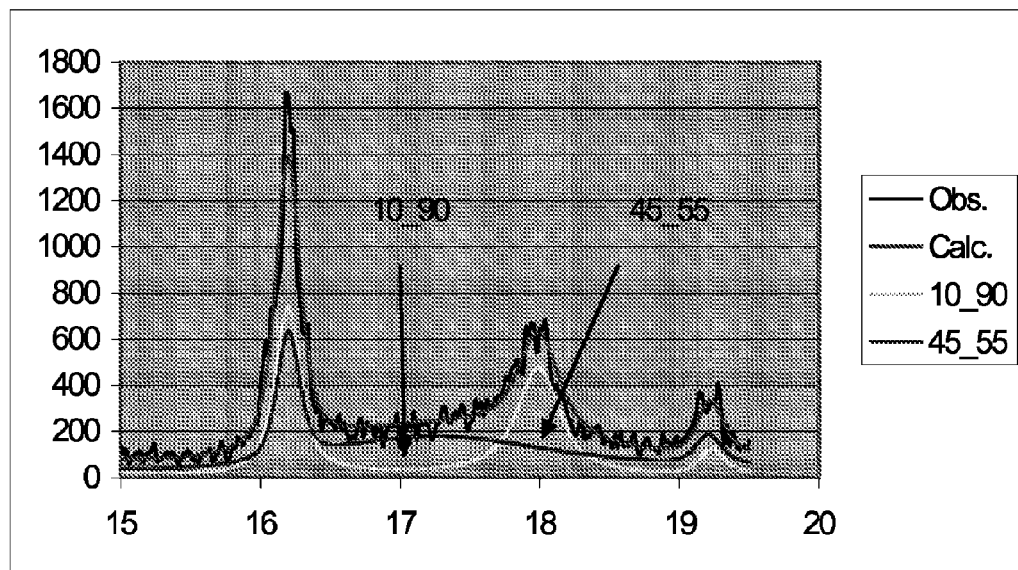
FIG. 6 is the XRD pattern of the material prepared in Example 9, which is a material with two AEI/CHA phases of different compositions; this material contains about 50% of a first phase having an AEI/CHA ratio of about 10/90, and about 50% of a second phase having an AEI/CHA ratio of 45/55.

The materials of the present invention usually have two broad features in the range from about 16.6 to about 18.5 degrees 2θ, each broad feature being characteristic of the first or second AEI/CHA intergrown phase. FIG. 6 illustrates such a material, which has two such broad features. Without wishing to be bound to any theory, it is believed that the first broad feature centered at about 16.9 degrees 2θ is indicative of an AEI/CHA phase having an AEI/CHA ratio of from about 30/70 to about 55/45 (in FIG. 6, of about 45/55), while the second broad feature centered at about 18 degrees 2θ is believed to be indicative of an AEI/CHA phase having an AEI/CHA ratio of from about 5/95 to about 40/60 (in FIG. 6, of about 10/90). The ratio of the first and second intergrowth phase is determined by best curve fitting, for varying ratios of the first to the second intergrowth phase. The ratio of the first to the second intergrowth phase may vary within broad limits, including from about 10:90 to about 90:10, preferably from about 30:70 to about 70:30, more preferably from about 40:60 to about 60:40. For the material of FIG. 6, this ratio is determined at 50:50. Preferably the CHA molecular sieve is SAPO-34 and the AEI molecular sieve is selected from SAPO-18, ALPO-18 and mixtures thereof.

The materials of the present invention have an overall AEI/CHA ratio which is obtained by weighing the contribution of each intergrowth phase. The overall AEI/CHA ratios calculated in this fashion range from about 20:80 to about 40:60, such as from about 25:75 to about 35:65. For the material of FIG. 6, such weighed average AEI/CHA ratio is of 28/72.

The silicoaluminophosphate of the present invention has a silica to alumina molar ratio (Si/Al$_2$) from about 0.13 to about 0.24, for example from about 0.15 to about 0.22, such as from about 0.17 to about 0.21, such as about 0.18 or about 0.19. The silica to alumina molar ratio is conveniently determined by chemical analysis.

The silicoaluminophosphate molecular sieve of the present invention may conveniently be prepared by a process that comprises:

a) combining a reactive source of silicon, a reactive source of phosphorus and a reactive source of aluminum in the presence of an organic structure directing agent (template) to form a mixture having a molar composition within the following ranges:
  P$_2$O$_5$: Al$_2$O$_3$ from about 0.6 to about 1.2,
  SiO$_2$: Al$_2$O$_3$ from about 0.10 to about 0.20,
  H$_2$O: Al$_2$O$_3$ from about 25 to about 50;

b) mixing and heating the mixture (a) to a crystallization temperature, such as between about 150° C. and about 220° C., typically between about 155° C. and about 200° C., preferably between about 165° C. and about 190° C.;

c) maintaining the mixture at the crystallization for a period of time of from about 2 to about 150 hours; and (d) recovering said molecular sieve.

The crystallization time in step c) will vary depending on the crystallization temperature, but the crystallization time should be sufficient to obtain substantially complete crystallization. For temperatures of from about 155° C. to 175° C., crystallization times from about 30 hours to about 150 hours are usually adequate.

Preferably, the mixture prepared at step a) has a molar composition within the following ranges:
  P$_2$O$_5$: Al$_2$O$_3$ from about 0.8 to about 1.1,
  SiO$_2$: Al$_2$O$_3$ from about 0.12 to about 0.15,
  H$_2$O: Al$_2$O$_3$ from about 35 to about 45.

It will be understood that the molar ratio of silica to alumina in the reaction mixture determines the silica to alumina ratio of the resultant molecular sieve although in general the molecular sieve is more silica-rich than the reaction mixture.

The reactive source of silicon used in the above mixture may be a silicate, e.g., fumed silica, such as Aerosil (available from Degussa), a tetraalkyl orthosilicate, or an aqueous colloidal suspension of silica, for example that sold by E.I. du Pont de Nemours under the tradename Ludox.

The reactive source of phosphorus used in the above mixture is conveniently phosphoric acid.

Examples of suitable reactive aluminum sources include hydrated aluminum oxides such as boehmite and pseudoboehmite. Preferably, pseudoboehmite is used.

The organic structure directing agent conveniently includes a tetraethyl ammonium compound, such as tetraethyl ammonium hydroxide (TEAOH), tetraethyl ammonium phosphate, tetraethyl ammonium fluoride, tetraethyl ammonium bromide, tetraethyl ammonium chloride or tetraethyl ammonium acetate. Typically, the directing agent includes tetraethyl ammonium hydroxide. In some cases, more than one organic structure directing agent may be employed, such as a combination of a tetraethyl ammonium compound and dipropylamine.

The amount of organic structure directing agent is typically such that the molar ratio of directing agent to alumina is from about 0.6 to about 1.2, such as from about 0.7 to about 1.1.

It is believed that the crystallization process to produce the molecular sieve of the present invention proceeds through the formation of a (silico)aluminophosphate precursor, having the structure of AlPO—H$_3$, variscite or metavariscite, during heat-up of the mixture, followed by dissolution of the precursor as the molecular sieve of the invention nucleates. Among the factors which influence the crystallization process to produce molecular sieve of the invention are the rate at which the mixture is heated and the rate at which the mixture is agitated at least during formation of the precursor. In particular, crystallization of the desired molecular sieve is enhanced if the heating rate is at least 8° C./hour, such as at least 10° C./hour. Typically the heating rate is from about 10° C./hour to about 40° C./hour, such as from about 15° C./hour to about 40° C./hour.

Preferably, the synthesis mixture is agitated (i.e. mixed, stirred, tumbled, shaken, swung or any other mode of agitation) while the reaction mixture is heated up to the crystallization temperature. Agitation is applied with an intensity that avoids precipitation of the synthesis mixture components. Hence the intensity of agitation may vary, depending on the physical and chemical nature of the components. Optionally, agitation may also be applied during all or part of the crystallization period.

In one practical embodiment, the crystallization process of the invention comprises at least two stages; namely a first stage in which the (silico)aluminophosphate precursor material is produced and a second stage in which the precursor material is converted into the desired intergrown AEI/CHA framework type molecular sieve. In the first stage, the synthesis mixture is heated under agitation so as to raise its temperature at said rate of at least 8° C./hour to a first temperature of about 99° C. to about 150° C., such as about 115° C. to about 125° C. The synthesis mixture is then maintained at said first temperature, preferably with the agitation being continued, for a time, typically from about 0.5 hours to about 120 hours, to form an intermediate product mixture containing a slurry of the precursor material. The intermediate product mixture is then heated so as to raise its temperature at a rate of at least 8° C./hour, such as at a rate of from about 10° C./hour to about 40° C./hour, to a second temperature generally from about 150° C. to about 220° C., such as about 165° C. to about 190° C. This second heating step can be conducted under static conditions or with reduced agitation as compared with the first heating step. The second synthesis mixture is then maintained at said second temperature until the intergrown molecular sieve crystallizes from the mixture, which generally takes from about 2 to about 150 hours; such as from about 5 to about 100 hours, for example from about 10 to about 50 hours.

Synthesis of the new intergrowth may be facilitated by the presence of at least 0.1 ppm, such as at least 10 ppm, for example at least 100 ppm, conveniently at least 500 ppm of seed crystals based on total weight of the reaction mixture. The seed crystals can be homostructural with the crystalline material of the present invention, for example the product of a previous synthesis, or can be a heterostructural crystalline material, such as an AEI, LEV, CHA or ER1 framework-type molecular sieve.

Typically, the crystalline product is formed in solution and can be recovered by standard means, such as by centrifugation or filtration. Typically the separation of the crystalline product from the crystallization mixture leaves a mother liquor, at least part of which can be recycled to step (b) thereby enhancing the yield of intergrowth per gram of template. Where the crystallization process is conducted in two stages, it is preferred to recycle the mother liquor to the second stage, namely by adding the mother liquor to the intermediate product mixture containing the precursor material. The separated product can also be washed, recovered by centrifugation or filtration and dried. The crystalline product is typically in the form of plates, platelets, stacked platelets or cubes. Typically the crystals have a $d_{50}$ (50% by volume of crystals is smaller than the $d_{50}$ value) particle size from about 0.1 to about 3 μm, such as about 0.5 to about 2.0 μm, for example about 1.3 to about 1.9 μm.

As a result of the crystallization process, the recovered crystalline product contains within its pores at least a portion of the organic directing agent used in the synthesis. In a preferred embodiment, activation is performed in such a manner that the organic directing agent is removed from the molecular sieve, leaving active catalytic sites within the microporous channels of the molecular sieve open for contact with a feedstock. The activation process is typically accomplished by calcining, or essentially heating the molecular sieve comprising the template at a temperature of from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agent from the intracrystalline pore system. In other cases, particularly with smaller organic directing agents, complete or partial removal from the sieve can be accomplished by conventional desorption processes.

Once the intergrown crystalline material of the invention has been synthesized, it can be formulated into a catalyst composition by combination with other materials, such as binders and/or matrix materials that provide additional hardness or catalytic activity to the finished catalyst.

Materials which can be blended with the intergrown crystalline material of the invention can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of intergrown crystalline material contained in the final catalyst product ranges from 10 to 90 weight percent of the total catalyst, preferably 20 to 80 weight percent of the total catalyst.

The intergrown crystalline material described herein can be used to dry gases and liquids; for selective molecular separation based on size and polar properties; as an ion-exchanger; as a catalyst in organic conversion reactions, such as cracking, hydrocracking, disproportionation, alkylation, isomerization, oxidation and synthesis of monoalkylamines and dialkylamines; as a chemical carrier; in gas chromatography; and in the petroleum industry to remove normal paraffins from distillates.

In particular, the intergrown crystalline material described herein is useful in the catalytic conversion of oxygenates to one or more olefins, particularly ethylene and propylene. Thus, according to the present invention, it has now been found that, with a silicoaluminophosphate molecular sieve comprising at least first and second intergrown phases of a CHA framework type material and an AEI framework type material, wherein said first intergrown phase has an AEI/CHA ratio of from about 5/95 to about 40/60 as determined by DIFFaX analysis and the second intergrown phase has an AEI/CHA ratio of about 30/70 to about 55/45 as determined by DIFFaX analysis, selecting the silica/alumina ratio of the sieve to be from about 0.13 to about 0.24, preferably from about 0.15 to about 0.22, more preferably from about 0.17 to about 0.21, such as about 0.18 or about 0.19, allows both the POS and POR to be maximized when the material is used in the conversion of oxygenates to olefins.

In addition, the materials of the invention having a silica/alumina ratio within this optimum range are found to exhibit excellent hydrothermal stability, as discussed in detail in U.S. Patent Application Publication No. 2004/0260140, published Dec. 23, 2004, fully incorporated herewith. In particular, the molecular sieve of the invention is found to retain at least 40%, such as at least 45%, of its activity for the conversion of oxygenates, such as methanol, to ethylene and propylene after being treated at 700° C. for 30 days in a nitrogen atmosphere comprising steam at a partial pressure of 13 psi (90 kPa).

As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4$-$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid;

n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In the present oxygenate conversion process, a feedstock comprising an organic oxygenate, optionally with one or more diluents, is contacted in the vapor phase in a reaction zone with a catalyst comprising the molecular sieve of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example from about 250° C. to about 800° C., including from about 250° C. to about 750° C., conveniently from about 300° C. to about 650° C., typically from about 350° C. to about 600° C. and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about 0.01 hr$^{-1}$ to about 500 hr$^{-1}$, such as in the range of from about 0.5 hr$^{-1}$ to about 300 hr$^{-1}$, for example in the range of from about 0.1 hr$^{-1}$ to about 200 hr$^{-1}$.

A practical embodiment of a reactor system for the oxygenate conversion process is a circulating fluid bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example air, to burn off coke from the catalyst, which restores the catalyst activity. The conditions of temperature, oxygen partial pressure, and residence time in the regenerator should be selected to achieve a coke content on the regenerated catalyst of less than about 0.5 wt %. At least a portion of the regenerated catalyst should be returned to the reactor.

The invention will now be more particularly described with reference to the following Examples.

In the examples, DIFFaX analysis was used to determine the AEI/CHA ratio of the molecular sieves. Simulated powder XRD diffraction patterns for varying ratios of AEI/CHA were generated using the DIFFaX program available from the International Zeolite Association (see also M. M. J. Tracey et al., Proceedings of the Royal Chemical Society, London, A (1991), Vol. 433, pp. 499-520 "Collection of Simulated XRD Powder Patterns for Zeolites" by M. M. J. Treacy and J. B. Higgins, 2001, Fourth Edition, published on behalf of the Structure Commission of the International Zeolite Association). The DIFFaX input file used to simulate the XRD diffraction patterns is given in Table 2 of U.S. Pat. No. 6,812,372, incorporated herein by reference. In order to obtain best fitting between the DIFFaX simulated patterns and the experimental patterns, two sets of simulated XRD patterns were generated using a line broadening of 0.009 (as described in U.S. Pat. No. 6,812,372) and a line broadening of 0.04 (FIGS. 1a and 1b). The simulated diffraction patterns were then compared with the experimental powder XRD diffraction patterns. In this respect, the most sensitive range is the 15 to 19.5 2θ range.

Example 1

A mixture of 382.39 g of phosphoric acid (85% in water, Acros), 371.99 g of demineralized water and 706.79 g of tetraethylammonium hydroxide solution (35% in water, Sachem) was prepared in a 2 liter polyethylene bottle. The resultant mixture was then transferred to a glass beaker placed in a Neslab bath at 30° C. and, after initiating stirring of the mixture with a laboratory mixer, 29.83 g Ludox AS 40 (40% silica) was added to the beaker followed by 227.01 g of alumina (Condea Pural SB-1). A slurry was produced and was then aged for 2 hours in the Neslab bath at 30° C. with the stirring being continued. The composition of the mixture in terms of molar ratios was as follows:

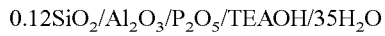

The mixture was transferred to a 2 liter PARR stainless steel autoclave and heated at a rate of 20° C./hour to 165° C. The mixture was stirred with a laboratory mixer at 200 rpm (tip speed of 1.3 m/s) during the whole hydrothermal treatment. The autoclave was kept at 165° C. for 60 hours. After cooling to room temperature, the slurry was washed. The washed slurry had a $d_{50}$ particle size of 1.8 μm, as measured with a Malvern Mastersizer 2000 ($d_{50}$ expressed by volume). The washed slurry was then dried and an X-ray diffraction pattern of the crystalline product was taken after the calcination procedure described above. Using this diffraction pattern, DIFFaX analysis was conducted and showed the crystalline product to contain two AEI/CHA intergrowths: 52% of an intergrown phase having an AEI/CHA ratio of 10/90 and 48% of an intergrown phase having an AEI/CHA ratio of 45/55, for an overall weighed AEI/CHA ratio of 27/73. The silica to alumina molar ratio (Si/Al$_2$) of the crystalline product was found to be 0.16.

Examples 2 to 11

THE procedure of Example 1 was repeated but with the amounts of the starting materials being adjusted to produce reaction mixtures having the silica to alumina molar ratios (Si/Al$_2$) set out in Table 2 below. Crystallization was conducted in the same manner as described in Example 1 although in some cases, as shown in Table 2, the crystallization time was increased to 72 hours. The silica to alumina molar ratios, d$_{50}$ particle sizes of the washed slurries and the AEI/CHA ratios of the final products are also given in Table 2.

TABLE 2

| Example | (Si/Al$_2$) Mix | Cryst. Time (hrs) | (Si/Al$_2$) Product | AEI/CHA Phase 1 | AEI/CHA Phase 2 | AEI/CHA Overall | d$_{50}$ μm |
|---|---|---|---|---|---|---|---|
| 1 | 0.12 | 60 | 0.16 | 10/90 52% | 45/55 48% | 27/73 | 1.8 |
| 2 | 0.10 | 60 | 0.13 | 10/90 50% | 45/55 50% | 27/73 | 1.9 |
| 3 | 0.11 | 60 | 0.14 | n/a* | n/a | n/a | 1.8 |
| 4 | 0.12 | 72 | 0.16 | 10/90 55% | 45/55 45% | 26/74 | 1.7 |
| 5 | 0.13 | 60 | 0.18 | 10/90 47% | 45/55 53% | 28/72 | 1.8 |
| 6 | 0.14 | 60 | 0.18 | 10/90 46% | 45/55 54% | 27/73 | 1.7 |
| 7 | 0.15 | 60 | 0.19 | n/a | n/a | n/a | 1.5 |
| 8 | 0.15 | 72 | 0.19 | n/a | n/a | n/a | 1.7 |
| 9 | 0.15 | 72 | 0.19 | 10/90 50% | 45/55 50% | 28/72 | 2.0 |
| 10 | 0.20 | 60 | 0.23 | 10/90 48% | 45/55 52% | 28/72 | 1.4 |
| 11 | 0.20 | 72 | 0.22 | 10/90 55% | 45/55 45% | 26/74 | 1.4 |

*n/a—not available

Example 12

A sample of each of the crystalline materials from Examples 2 to 11 was loaded into a fixed bed reactor equipped with an on-line gas chromatograph and was used to convert a methanol-containing feed at a temperature of 450° C.; a WHSV between 800 and 1000 hr$^{-1}$ and a methanol partial pressure of 40 psia (276 kPa). The methanol conversion activity of each of the materials, as the first order rate constant $K_{max}$ at the point at which the average methanol conversion was reached, was calculated according to the following equation:

$$K_{max}(Hz) = -\ln(1-Xm)/\tau$$

where Xm is the maximum conversion of methanol, and τ is space time(sec).

Figure 3A:
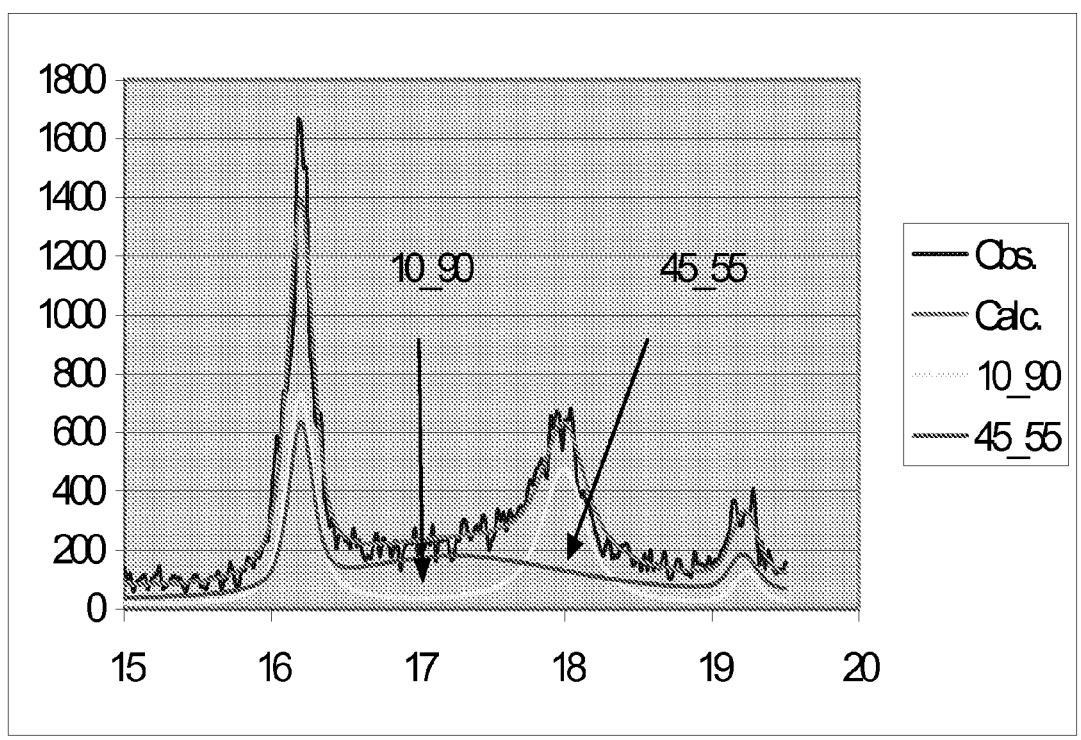
FIGS. 3a and 3b are graphs comparing the methanol conversion activity (Kmax) of the silicoaluminophosphate molecular sieves produced in Examples 2 to 11 with their silica to alumina ratio (Si/Al$_2$) ratio and with their POS and POR.

The calculated $K_{max}$ values are plotted against the Si/Al$_2$ of each sieve in FIG. 3a.

Example 13

A further sample of each of the crystalline materials from Examples 2 to 11 was loaded into a fixed bed reactor equipped with an on-line gas chromatograph and was used to convert a methanol-containing feed at a temperature 475° C.; a WHSV of 100 hr 1 and a pressure of 40 psia (276 kPa). The average POS and POR values of the resultant products were measured and the results are plotted against the Si/Al$_2$ of each sieve in FIG. 3b.

Figure 3B:
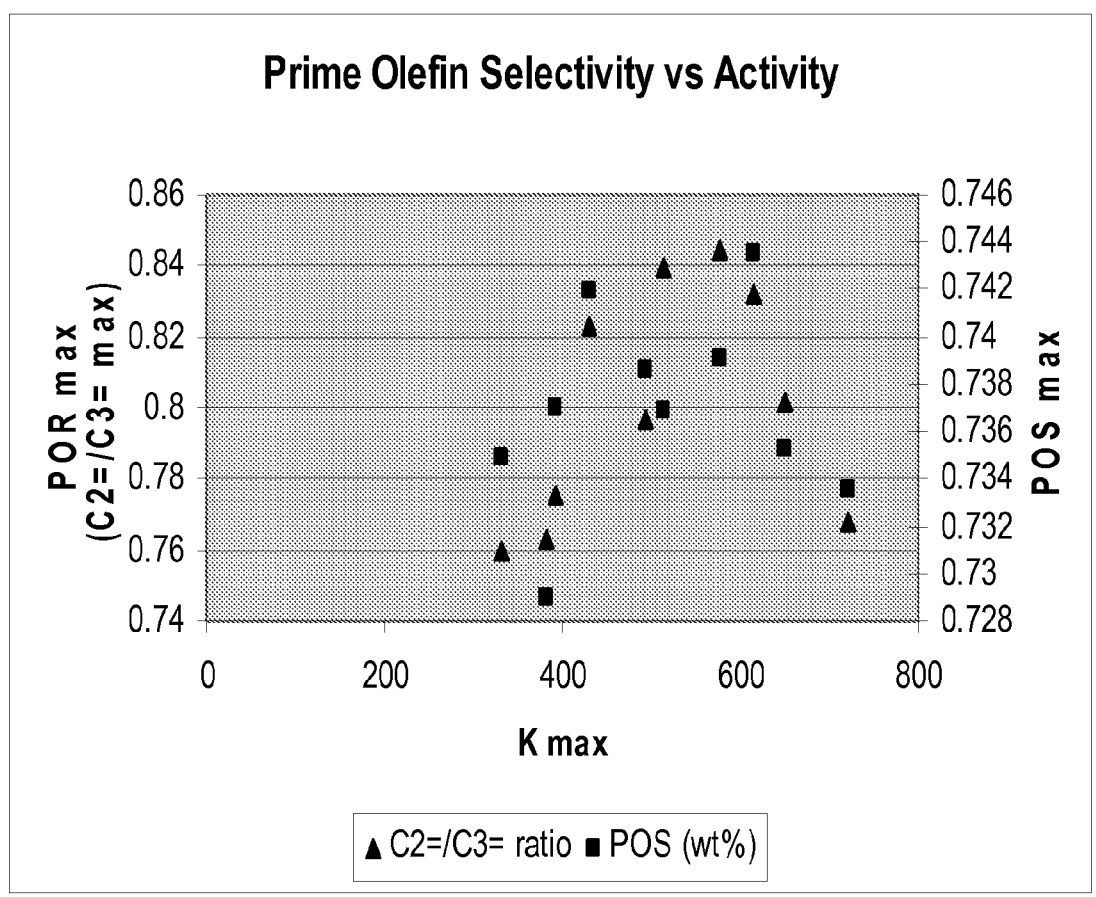
Figure 4:
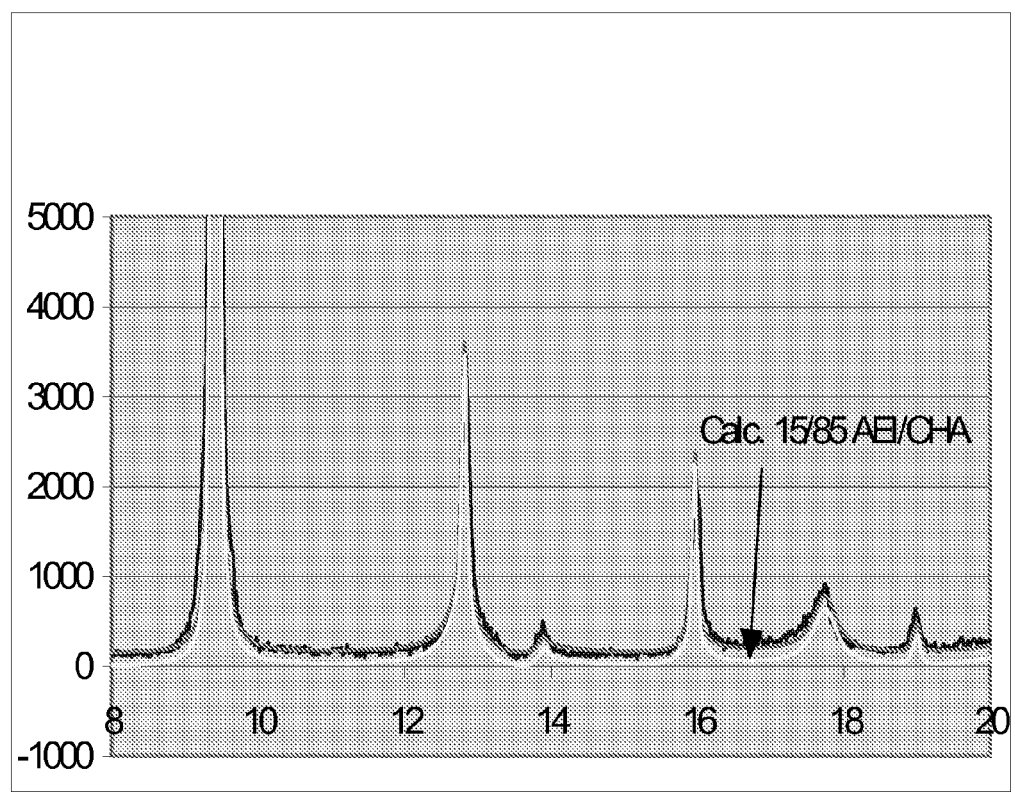
FIG. 4 is the XRD pattern of a single intergrown phase material having an AEI/CHA ratio of about 15/85 with an overlay of a DIFFaX simulated pattern.
Figure 5:
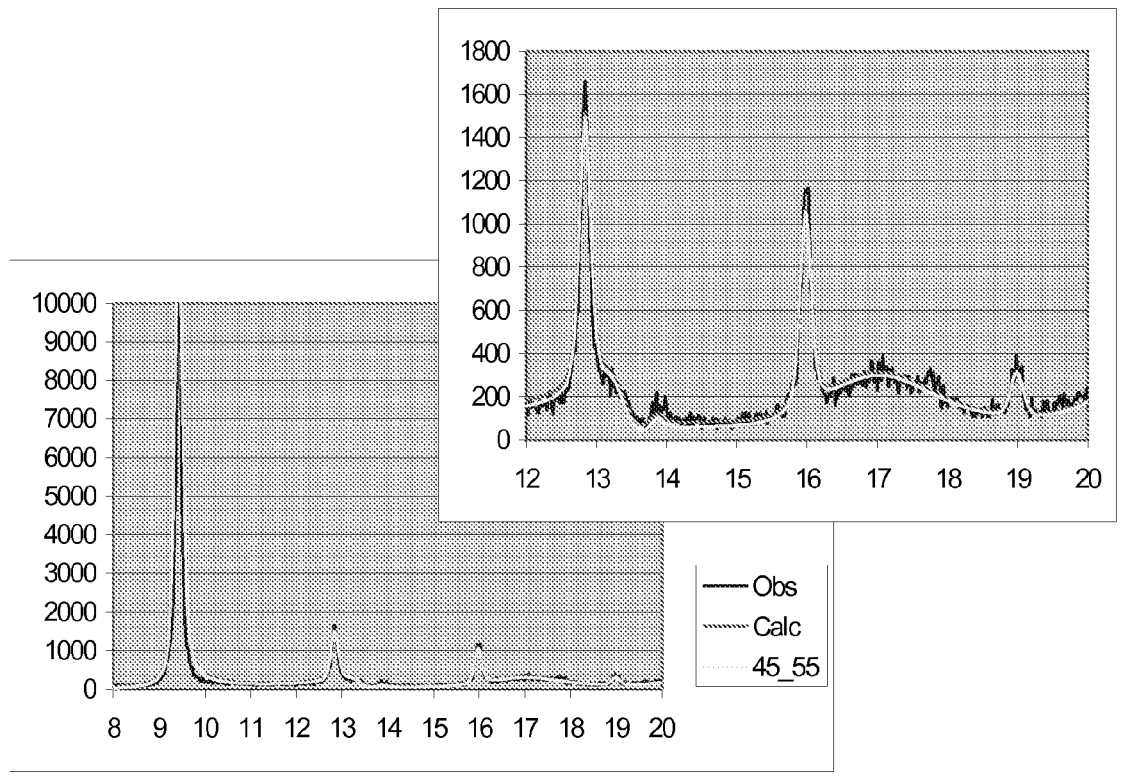
FIG. 5 is the XRD pattern of a single intergrown phase material having an AEI/CHA ratio of about 45/55 with an overlay of a DIFFaX simulated pattern.

Comparing FIGS. 3a and 3b, it will be seen that both the POS and POR values reach an optimum at a $K_{max}$ value of from about 400 to 650 Hz.

Example 14

The molecular sieves of Examples 4 and 10, together with an AEI/CHA intergowth having the same Si/Al$_2$ as the material of Example 3 were formed into catalysts as follows.

An aqueous slurry was produced comprising 45 wt % solids wherein the solids comprised 40 wt % of the sieve, 12 wt % of an alumina binder derived from aluminum chlorohydrate supplied under the trade name Microdry by Reheis Inc., Berkeley Heights, N.J., USA, and 48 wt % of kaolin clay supplied under the trade name Hydrite Ultrafine by Imerys, Roswell, Ga., USA. The slurry was dried and then calcined at 650° C. to produce the finished catalyst.

The hydrothermal stability of each catalyst was determined by measuring methanol conversion activity of the catalyst before and after the catalyst had been subjected to an accelerated steam deactivation test.

The accelerated steam deactivation test was conducted by loading 2.0 g of the catalyst between stacks of quartz fiber felt in a 0.375 inch (0.95 cm) internal diameter tubular alloy reactor and then filling the remainder of the reactor with silicon carbide particles. A gas mixture of nitrogen and steam was then flowed over the catalyst at 300 cc/minute at 700° C. for 30 days at a steam partial pressure of 13 psi (90 kPa).

The methanol conversion activity of each catalyst was measured in a laboratory micro-reactor. An amount of 10-30 mg of the catalyst particles mixed with 50-150 mg of silicon carbide was loaded in a stainless steel tube having an outside diameter of ¼ inch (0.63 cm). The catalyst was positioned between two stacks of quartz fiber frit and methanol was brought in contact with the catalyst to reactor at 450° C. and 25 psi (172 kPa) and a WHSV of 400 hr$^{-1}$ (WHSV based on the amount of molecular sieve in the catalyst). The product stream was analyzed by an on-line Agilent 6890 gas chromatograph equipped with a fast module LTM A58 using a LOWOX DI-C300 10M×0.53 mm column from RVM Scientific, Inc., Santa Barbara, Calif. The activity of each catalyst, $K_{max}$ (as defined in Example 12), before and after steam deactivation is shown in Table 3 below.

TABLE 3

| Example | Si/Al$_2$ | Initial $K_{max}$ | $K_{max}$ after steaming | Loss of activity (%) |
|---|---|---|---|---|
| 3 | 0.14 | 113.4 | 44.4 | 60.8 |
| 4 | 0.16 | 296.9 | 194.1 | 34.6 |
| 10 | 0.23 | 306 | 237.4 | 22.4 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A silicoaluminophosphate molecular sieve comprising first and second intergrown phases of a CHA framework type and an AEI framework type, wherein said first intergrown phase has an AEI/CHA ratio of from about 5/95 to about 40/60 as determined by DIFFaX analysis, the second intergrown phase has an AEI/CHA ratio of about 30/70 to about 55/45 as determined by DIFFaX analysis, wherein the ratio of first to second intergrown phase is from about 30:70 to about 70:30; and wherein said molecular sieve has a silica to alumina molar ratio ($SiO_2:Al_2O_3$) from 0.17 to about 0.24.

2. The silicoaluminophosphate molecular sieve of claim 1, wherein said first intergrown phase has an AEI/CHA ratio of from about 5/95 to about 20/80.

3. The silicoaluminophosphate molecular sieve of claim 2, wherein said second intergrown phase has an AEI/CHA ratio of from about 40/60 to about 50/50.

4. The silicoaluminophosphate molecular sieve of claim 1, wherein the ratio of first to second intergrown phase is from about 40:60 to about 60:40.

5. The silicoaluminophosphate molecular sieve of claim 1 and having an X-ray diffraction pattern having at least one reflection peak in each of the following ranges in the 5 to 25 (2θ) range:

| 2θ (CuKα) |
| --- |
| 9.3-9.6 |
| 12.7-13.0 |
| 13.8-14.0 |
| 15.9-16.1 |
| 17.7-18.1 |
| 18.9-19.1 |
| 20.5-20.7 |
| 23.7-24.0. |

6. The silicoaluminophosphate molecular sieve of claim 5, wherein said X-ray diffraction pattern has no reflection peak in the 9.8 to 12.0 (2θ) range.

7. The silicoaluminophosphate molecular sieve of claim 1, having an XRD pattern exhibiting two broad features in the 16.6 to 18.5 (2θ) range.

8. The silicoaluminophosphate molecular sieve of claim 7, wherein said first broad feature is centered at about 17 (2θ) and said second broad feature is centered at about 18 (2θ).

9. The silicoaluminophosphate molecular sieve of claim 1, and having a $d_{50}$ particle size of about 0.1 to about 3 μm.

* * * * *